(12) United States Patent
Miller et al.

(10) Patent No.: US 10,888,511 B2
(45) Date of Patent: Jan. 12, 2021

(54) METHODS AND ARTICLES OF MANUFACTURE FOR THE TREATMENT OF SKIN

(71) Applicant: Advanced Collagen Science LLC, Brookline, MA (US)

(72) Inventors: Leonard B. Miller, Brookline, MA (US); Dale P. Devore, Chelmsford, MA (US)

(73) Assignee: Advanced Collagen Science LLC, Brookline, MA (US)

( * ) Notice: Subject to any disclaimer, the term of this patent is extended or adjusted under 35 U.S.C. 154(b) by 0 days.

(21) Appl. No.: 15/819,807

(22) Filed: Nov. 21, 2017

(65) Prior Publication Data

US 2018/0153787 A1   Jun. 7, 2018

Related U.S. Application Data

(63) Continuation of application No. 14/782,420, filed as application No. PCT/US2014/032951 on Apr. 4, 2014, now abandoned.

(60) Provisional application No. 61/808,967, filed on Apr. 5, 2013.

(51) Int. Cl.
| | |
|---|---|
| *A61K 8/35* | (2006.01) |
| *A61K 8/49* | (2006.01) |
| *A61Q 19/00* | (2006.01) |
| *A61Q 19/08* | (2006.01) |

(52) U.S. Cl.
CPC .............. *A61K 8/498* (2013.01); *A61K 8/35* (2013.01); *A61Q 19/00* (2013.01); *A61Q 19/08* (2013.01); *A61K 2800/28* (2013.01); *A61K 2800/87* (2013.01); *A61K 2800/882* (2013.01); *A61K 2800/884* (2013.01); *A61K 2800/91* (2013.01); *A61K 2800/94* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 5,248,693 | A | 9/1993 | Gerspacher et al. |
| 5,368,581 | A | 11/1994 | Smith et al. |
| 5,439,954 | A | 8/1995 | Bush |
| 2005/0106270 | A1 | 5/2005 | Devore et al. |
| 2009/0177171 | A1* | 7/2009 | Ignon .................... A61B 17/54 |
| | | | 604/289 |
| 2011/0259974 | A1 | 10/2011 | Cooper et al. |

FOREIGN PATENT DOCUMENTS

| | | |
|---|---|---|
| WO | 2002/17936 A1 | 3/2002 |
| WO | 2012/116445 A1 | 9/2012 |

OTHER PUBLICATIONS

Wermeling et al (PNAS, 2008, vol. 105, No. 6) (Year: 2008).*
U.S. Appl. No. 14/782,420, filed Oct. 5, 2015, 2016-0038391, Abandoned.
Farage et al., Intrinsic and extrinsic factors in skin ageing: a review. Int J Cosmet Sci. Apr. 2008;30(2):87-95.
Nakagawa et al., In vivo measurement of the water content in the dermis by confocal Raman spectroscopy. Skin Res Technol. May 2010;16(2):137-41.
Seehra et al., Viscoelastic properties of acid- and alkaline-treated human dermis: a correlation between total surface charge and elastic modulus. Skin Res Technol. Aug. 2006;12(3):190-8.
Silver et al., Viscoelastic properties of human skin and processed dermis. Skin Res Technol. Feb. 2001;7(1):18-23.
Stark, Recent developments in chemical modification and sequential degradation of proteins. Adv Protein Chem. 1970;24:261-308.
International Search Report and Written Opinion for Application No. PCT/US2014/032951, dated Oct. 27, 2014.

* cited by examiner

*Primary Examiner* — Jared Barsky
(74) *Attorney, Agent, or Firm* — Unikel Law LLC

(57) ABSTRACT

Embodiments of the present invention are directed to methods and articles of manufacture to treat skin to improve and/or increase hydration, pliability, and thickness for improved texture, feel and appearance. Embodiments feature applying an effective amount of an acetylation agent to natural dermal collagen under reaction conditions to react the natural dermal collagen with the acetylation agent to form a modified collagen. The modified collagen has a higher net charge and higher net charge density than natural dermal collagen. The modified collagen improves or increases one or more skin characteristics consisting of hydration, pliability and thickness.

24 Claims, 1 Drawing Sheet

METHODS AND ARTICLES OF MANUFACTURE FOR THE TREATMENT OF SKIN

RELATED APPLICATIONS

This application is a continuation of U.S. application Ser. No.: 14/782,420, filed Oct. 5, 2015, which is a 371 of International Patent Application No.: PCT/US2014/032951, which claims priority to U.S. Provisional Application Ser. No.: 61/808,967, filed Apr. 5, 2013. The entire contents of each application are incorporated herein by reference in their entirety.

FIELD OF THE INVENTION

The present invention relates to the treatment of skin and articles to effect the treatment of skin to increase hydration, pliability and thickness of skin, to improve its texture, feel and appearance.

BACKGROUND OF THE INVENTION

The aging causes changes in skin. These changes include dryness, wrinkling, laxity, uneven pigmentation, and a variety of proliferation lesions. Changes in dermis primarily include atrophy or loss of dermal volume, fewer fibroblasts, vessels, and mast cells, shorter capillary loops, and abnormal nerve endings. Loss of dermal thickness is about 20% in older individuals decreasing from an average of about 1.1 mm at the age of 20 to about 0.8 mm at the age of 80.

It is commonly assumed that aged skin is intrinsically less hydrated, less elastic, more permeable and more susceptible to irritation, because of an apparently less complete functional barrier measured by higher transepidermal water loss [Intrinsic and extrinsic factors in skin ageing: a review M. A. Farage*, K. W. Miller*, P. Elsner, and H. I. Maibach, International Journal of Cosmetic Science, 2008, 30, 87-95].

It would be useful to have methods and articles of manufacture to treat skin to improve and/or increase hydration, pliability, and thickness for improved texture, feel and appearance.

SUMMARY OF THE INVENTION

As used herein, the term "natural dermal collagen" refers to the collagen as it is normally and naturally found in the dermis layer of skin. A "modified collagen" refers to a collagen that has reacted with the acetylation agent and bears a higher net charge or a higher net charge density due to the modification than the normal natural collagen. By "acetylation agent" is meant an agent that transfers an acyl group to another nucleophile. Examples of acetylation agents are sulfonic acids, anhydrides, sulfonyl chlorides, and acid chlorides.

The skin characteristics of improved hydration, pliability and thickness may not be immediate. The hydration caused or effected by the modified collagen may take place after time allowing for the perfusion of fluids and the like. An effective amount of an acetylation agent may have multiple applications over a period of time, to effect small incremental changes in the nature of daily or weekly applications, or may be effected in a single application.

One embodiment of the method features the step of treating the area of the skin receiving the acetylation agent to allow penetration of the acetylation agent through the stratum corneum and epithelium of the skin. For example, without limitation, embodiments of the present invention feature one or more skin preparation treatments selected from the group consisting of dermal abrasion, micro-needle puncture, abrasive washes and air jet injection. Air jet injection can be used to deliver the acetylation agent and/or treat the skin to make the skin more permeable to the acetylation agent.

Embodiments of the present method feature an effective amount of an acetylation agent is in a deliver system. By way of example, without limitation, embodiments of the present invention feature foams, ointments, pastes, oils, creams, solutions, tinctures, gels, suspensions, powders, aerosols and emulsions. The air jet injection, discussed earlier, works with a solution of the acetylation agent.

Embodiments of the present method feature deliver system having an aqueous base. As used herein the term "aqueous base" refers to having a substantial water component, as in emulsions, solutions, creams, some gels, some suspensions and foams. One embodiment features an acetylation agent in an aqueous base, buffered at a pH of 8.0 to 10.0. The buffer maintains the acetylation agent in a reactive form.

Other embodiments of the invention feature a deliver system having an oil base. As used herein the term "oil base" refers to having a substantial oil component. The oil component may be a petroleum based oil, such as mineral oil or petrolatum jelly, or the oil may be derived from animal or plant sources, such as vegetable oil, canoba oil, corn oil, cottonseed oil, sesame oil and the like. Oils can also be described or characterized as natural or synthetic. By "natural oil" is meant glycerol esters composed of glycerol and fatty acids and include coconut oil, corn oil, olive oil and other such oils. By "synthetic oil" is meant esters usually prepared by reaction of fatty acids with alcohols and include white oil, isopropyl ester oil, ethylhexyl ester oil, stearyl ester oil, oleic ester oil, and other such oils. The oil normally will not solubilize the acetylation agent, and the acetylation agent is held as a suspension.

One embodiment of the present invention features an alcohol base. As used herein the term "alcohol base" refers to a substantial alcohol component, in the sense of a tincture. The alcohol component allows solubilization of the acetylation agent in the absence of water and is not as likely to promote degradation of the acetylation product into inactive forms.

The method of the present invention feature delivery systems, either aqueous based, oil based or alcohol based having a concentration of acetylation agent of 1-100 mg/ml, and, more preferably, 10-80 mg/ml or 30-50 mg/ml.

Embodiments of the present invention feature a delivery system having a penetration enhancer. Examples of penetration enhancers are, without limitation ethylenediaminetetraacetic acid and salts thereof, dimethyl sulfoxide, fatty alcohols fatty acid esters, fatty acids, fatty alcohol esters, surfactants, N-methyl pyrrolidones, ionic compounds, and addition compounds listed in Pharmaceutical Technology November 1997. One embodiment features ethylenediaminetetraacetic acid present in a concentration of 0.022 M to 0.040 M.

A further embodiment of the method comprises one or more post application treatments such as the application of washes. The wash or washes are selected from the group of solutions consisting of aqueous solutions, phosphate buffered solutions, saline solutions and surfactant solutions and combinations thereof.

The acetylation agent of the present method is selected from the group consisting of maleic anhydride, succinic anhydride, glutaric anhydride, citractonic anhydride, methyl succinic anhydride, itaconic anhydride, methyl glutaric anhydride, dimethyl glutaric anhydride, phthalic anhydride, oxalyl chloride, malonyl chloride, chlorosulfonylacetyl chloride, chlorosulfonylbenzoic acid, 4-chloro-3-(chlorosulfonyl)-5-nitrobenzoic acid, 3-(chlorosulfonyl)-P-anisic acid, 3-sulfobenzoic acid, 3,5-dicarboxybenzenesulfonyl chloride, acetic anhydride, chloroacetic anhydride, propionic anhydride, butyric anhydride, isobutyric anhydride, isovaleric anhydride, hexanoic anhydride, acetyl chloride, propionyl chloride, dichloropropionyl chloride, butyryl chloride, isobutyryl chloride, valeryl chloride, ethane sulfonyl chloride, methane sulfonyl chloride, 1-butane sulfonyl chloride, 4,6-diamino-2-methylthiopyrimidine-5-sulfonic acid, and mixtures and combinations thereof.

Embodiments of the present method feature the acetylation agent glutaric anhydride or a methyl derivative thereof applied to the natural dermal collagen in an aqueous base at a pH of 8.0-10. Other embodiments feature agent glutaric anhydride or a methyl derivative thereof held in an oil base.

A further embodiment of the present invention is directed to an article of manufacture. The article of manufacture is a delivery system for the treatment of skin. The delivery system has an effective amount of an acetylation agent to apply to natural dermal collagen under reaction conditions to react with the natural dermal collagen to form a modified collagen. The modified collagen has a higher net charge and higher net charge density than natural dermal collagen. The modified collagen increases or improves one or more skin characteristics consisting of hydration, pliability and thickness.

As used herein, the term "article of manufacture" refers to a formula, kit, cosmetic or medicament. Kits typically have one or more of the following items such as, without limitation, containment vessels for holding medicaments and/or cosmetic formulations, devices for their application to an individual and instructions for their use.

One embodiment of the article of manufacture of the present invention features penetration means for treating the area to allow penetration of the acetylation agent through the stratum corneum and epithelium of the skin. As used herein the term "penetration means" refers to one or more dermal abrasion elements, micro-needles, needles for injection, hollow micro-needles, abrasive washes and air jet injection sprays. Air injection sprays can also be used to directly administer the acetylation agent to the natural dermal collagen.

One embodiment of the article of manufacture of the present invention features deliver systems selected from the group consisting of transdermal patches, foams, ointments, pastes, oils, creams, solutions, tinctures, gels, suspensions, powders, aerosols and emulsions. The drug delivery systems comprise oil bases, aqueous bases, alcohol bases, emulsions, suspensions and solutions. Embodiments featuring an aqueous base hold the acetylation agent in a buffered solution at a pH of 8.0 to 10.0. A preferred concentration of the acetylation agent in alcohol, aqueous and oil bases is 1 to 100 mg/ml.

One embodiment features a delivery system having a penetration enhancer. Examples of penetration enhancers are, without limitation, ethylenediaminetetraacetic acid and salts thereof and dimethyl sulfoxide. One embodiment features ethylenediaminetetraacetic acid present in a concentration of 0.022 M to 0.040 M.

One embodiment of the present article of manufacture further comprising at least one post application treatment, such as, without limitation, a wash or washes. The wash is selected from the group of solutions consisting of aqueous solutions, phosphate buffered solutions, saline solutions and surfactant solutions and combinations thereof.

One embodiment of the article of manufacture features an acetylation agent is selected from the group consisting of maleic anhydride, succinic anhydride, glutaric anhydride, citractonic anhydride, methyl succinic anhydride, itaconic anhydride, methyl glutaric anhydride, dimethyl glutaric anhydride, phthalic anhydride, oxalyl chloride, malonyl chloride, chlorosulfonylacetyl chloride, chlorosulfonylbenzoic acid, 4-chloro-3-(chlorosulfonyl)-5-nitrobenzoic acid, 3-(chlorosulfonyl)-P-anisic acid, 3-sulfobenzoic acid, 3,5-dicarboxybenzenesulfonyl chloride, acetic anhydride, chloroacetic anhydride, propionic anhydride, butyric anhydride, isobutyric anhydride, isovaleric anhydride, hexanoic anhydride, acetyl chloride, propionyl chloride, dichloropropionyl chloride, butyryl chloride, isobutyryl chloride, valeryl chloride, ethane sulfonyl chloride, methane sulfonyl chloride, 1-butane sulfonyl chloride, 4,6-diamino-2-methylthiopyrimidine-5-sulfonic acid, and mixtures and combinations thereof.

The example of the Detailed Description feature the acetylation agent glutaric anhydride or a methyl derivative thereof held in oil, aqueous, and alcohol bases.

One embodiment of the present article of manufacture features an acetylation agent held in a first containment vessel and an aqueous base held in a second containment vessel. The acetylation agent and aqueous base are combined in a mixing unit immediately prior to administration to dermal collagen. The containment vessels may comprise vials syringes and foil packs. The article of manufacture may comprise administration tools such as a jet spray injector and pads.

These and other features and advantages of the present invention will be apparent so those skilled in the art upon viewing the figures which are described briefly in the next section and upon reading the Detailed Description that follows.

DETAILED DESCRIPTION OF THE INVENTION

Figure 1:
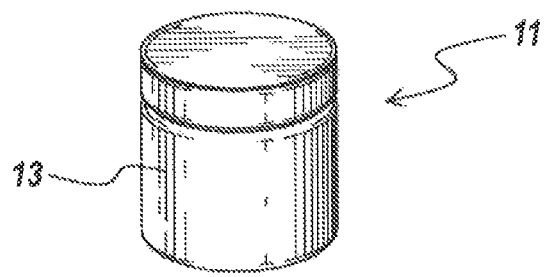
FIG. 1 depicts an article of manufacture embodying features of the present invention.

The present invention relates to a process for selectively treating in vivo animal tissue to alter its biomechanical properties. More particularly, this invention relates to a process for selectively treating skin dermal layers in vivo using acetylation chemistry to alter its biophysical properties. This process may be used to alter the net charge and net charge density on collagen molecules, collagen fibrils and collagen fibers resulting in an increase in dermal thickness and pliability.

The major aging changes in skin include dryness, wrinkling, laxity, uneven pigmentation, and a variety of proliferative lesions. Changes in dermis primarily include atrophy or loss of dermal volume, fewer fibroblasts, vessels, and mast cells, shorter capillary loops, and abnormal nerve endings. Loss of dermal thickness is about 20% in older individuals decreasing from an average of about 1.1 mm at the age of 20 to about 0.8 mm at the age of 80.

It is commonly assumed that aged skin is intrinsically less hydrated, less elastic, more permeable and more susceptible to irritation, because of an apparently less complete functional barrier measured by higher transepidermal water loss [Intrinsic and extrinsic factors in skin ageing: a review M. A. Farage*, K. W. Miller*, P. Elsner, and H. I. Maibach, International Journal of Cosmetic Science, 2008, 30, 87-95]

Water plays important roles in maintaining the condition of the skin. In the stratum corneum, water interacts with a natural moisturizing factor and keratin to give elasticity to the stratum corneum. In the dermis, the dermal fluid correlates with the skin elasticity. [Noriaki Nakagawa, Masayuki Matsumoto and Shingo Sakai. Skin Research and Technology 2010; 16:137-141]

The pH and charged residue dependency of the elastic modulus suggests that charged pair interactions and repulsions within and between collagen molecules are involved in elastic energy storage during stretching at high strains. [Gurinder P. Seehra and Frederick H. Silver Skin Research and Technology 2005; 11; 1-9]

Furthermore, biomechanical properties overall change during aging as the skin becomes increasing rigid, inelastic and slower to recover from compressive forces. A recent paper by Silver, F H, Seehra, G P, Freeman, J W and DeVore, D P (Skin Research & Technology, 2001) reports the disruption of the elastic fiber and loss of α-helical structure associated with aging skin.

Embodiments of the present invention improve dermal thickness and dermal elasticity by treating skin with agents that alter net charge and net charge density on dermal proteins, particularly collagen.

Acetylation Kinetics

Chemical agents will react with proteins to alter their chemical and physical characteristics. Generally, these chemical agents are used to modify proteins in solution. Several reviews discussing chemical modification are available including *Chemical Reagents for Protein Modification*, Ed. R L Lunblad, CRC Press, Boca Raton, 1991 and G R Stark, Recent developments in chemical modification and sequential degradation of proteins. Advances in Protein Chemistry, 24: 261-308, 1970. Specific chemical agents react with deprotonated free amines on proteins to replace the positive ($NH_3^+$) charge with a chemical moiety exhibiting a negative charge or neutral charge. Other chemical agents react with deprotonated amines on proteins to replace a single positive ($NH_3^+$) charge with two positive charges ($NH_3^+ \times 2$). This change in net charge and charge density alters both the chemical and physical characteristics of the protein.

In the present invention, detailed methods are described using acetylation chemistry to treat intact skin to alter the biophysical properties of dermal tissue. Reactivity with dermis, particularly dermal collagen, is facilitated by pre-treating intact skin using dermabrasion techniques to remove stratum corneum, and epithelium, or application of a micro-needle roller to create openings through the stratum corneum and epithelium. In addition, the present invention describes non-aqueous or lipophilic carriers containing acetylation agents that facilitate effective delivery of such compositions. Non aqueous or lipophilic carriers facilitate transport of acetylation agents through stratum corneum. The use of aqueous or hydrophilic carriers or solvents limits the effective delivery time of such compositions as the acetylation agents rapidly hydrolyze and become ineffective. The present invention also describes the use of skin penetration enhancers to facilitate delivery of acetylation agents to the dermal layer.

Effective acetylation agents include sulfonic acids, anhydrides, sulfonyl chlorides, and acid chlorides are classes of chemical compounds that react with free amines of proteins resulting in the covalent attachment of the specific chemical moieties to proteins. These compounds are commonly known as acetylation reagents.

Specific acetylation agents have been used to alter the net charge and charge density of intact tissue proteins. Certain agents can be used to change the net charge from positive to negative. These agents include, but are not limited to anhydrides including maleic anhydride, succinic anhydride, glutaric anhydride, citractonic anhydride, methyl succinic anhydride, itaconic anhydride, methyl glutaric anhydride, dimethyl glutaric anhydride, phthalic anhydride, and many other such anhydrides. Acid chlorides include, but are not limited to, oxalyl chloride, malonyl chloride, and many others. Sulfonyl chlorides include, but are not limited to, chlorosulfonylacetyl chloride, chlorosulfonylbenzoic acid, 4-chloro-3-(chlorosulfonyl)-5-nitrobenzoic acid, 3-(chlorosulfonyl)-P-anisic acid, and others. Sulfonic acid includes, but is not limited to, 3-sulfobenzoic acid and others.

Certain agents can change the net charge from one positive to two negatives per reacted site. Specific agents include, but are not limited to 3,5-dicarboxybenzenesulfonyl chloride and others.

Certain agents can be used to change the net charge from positive to neutral per reacted site. Specific agents include, but are not limited to, anhydrides including acetic anhydride, chloroacetic anhydride, propionic anhydride, butyric anhydride, isobutyric anhydride, isovaleric anhydride, hexanoic anhydride, and other anhydrides; acid chlorides including acetyl chloride, propionyl chloride, dichloropropionyl chloride, butyryl chloride, isobutyryl chloride, valeryl chloride, and others; sulfonyl chlorides including, but not limited to, ethane sulfonyl chloride, methane sulfonyl chloride, 1-butane sulfonyl chloride, and others.

Certain agents can be used to change the net charge from one positive to two positives per reacted site. Specific agents include, but are not limited to, 4,6-diamino-2-methylthio-pyrimidine-5-sulfonic acid, and others.

Effective non-aqueous or hydrophilic carriers or solvents for acetylation agents include oils and waxes such as white oils, isopropyl esters, stearyl/isocetyl esters, propoxylated alcohols, caprilic/carpic esters, oleic acid esters, polymer oils, and silicone oils.

Effective penetration enhancer carriers for acetylation agents include fatty alcohols, fatty acids, and other miscellaneous compounds listed in "Skin Penetration Enhancers Cites in the Technical Literature" (Osborne, D W and Henke, J J. Pharmaceutical Technology, November 1997)

Effective delivery of acetylation agents to dermal tissue results in alterations in the net charge or net charge density to improve the biophysical properties of skin, including increasing the thickness and pliability of aged skin.

The present invention is based on the discovery that chemical acetylation of the dermis of pre-treated intact skin to alter the net charge and net charge density of reacted tissues and tissue surfaces rejuvenates skin degenerated by aging and disease. Aspects of the present methods and articles of manufacture are improved with pre-treatment of intact skin or the inclusion of effective penetration enhancers to facilitate diffusion of acetylation agents through the stratum corneum and epithelium into the dermal skin layers.

The acetylation of dermal tissue using acetylation agents can increase the net negative charge density resulting in an increase in tissue thickness and an increase in both low and high modulus measured from stress-stain analysis. Increased modulus readings relate to increased stiffness of treated tissues and more force required compressing the treated tissues. The acetylation of dermal tissue using acetylation agents can decrease the net negative charge density resulting in negligible effect on tissue thickness but with dramatic reductions in low modulus data from stress-strain analysis. The latter relates to increased softening of treated tissue or less force required to compress the treated tissues.

The present invention features a process for reacting an acetylation agent with intact tissues or tissue surfaces to alter the net charge and net charge density of tissues for therapeutic applications.

For example, when applying the acetylation agent, glutaric anhydride (GA), it is desirable that the anhydride exhibit GA activity greater than 90% (the remaining being inactive glutaric acid). It is desirable to apply GA to tissue pretreated to deprotonate free amines on proteins. If applied in aqueous solution, it is desired to mix and apply GA to pretreated tissue within 5-15 seconds. If GA is applied in natural or synthetic oils, such oils protect the active GA from immediate hydrolysis into an inactive acid form. Turning now to FIG. 1, a delivery system, generally designated by the numeral 11, is depicted. The delivery system 11 has a containment vessel 13 holding GA in an oil base for application to the skin.

One method includes steps of (1) applying a pre-treatment step to the tissue surface such that the desired area of the tissue surface is exposed to treatment solutions (such as dermabrasion or micro-needle puncture); (2) pretreating the exposed tissue surface with slightly alkaline buffer solution for 30 seconds-2 minutes to bring the pH of the tissue surface to between 7.5 and 9.5 resulting in deprotonation of ε-amino groups of lysine residues on exposed proteins; (3) removing the pretreatment buffer solution using an absorbent sponge (optional); (4) applying the acetylation agent to the exposed area at a concentration of between 0.1 mg/mL and 100 mg/mL, preferably between 10 mg/mL and 50 mg/mL, mixed in an alkaline buffer or alkaline aqueous solution, at a higher concentration than that used in the pretreatment solution, or mixed in a natural or synthetic oil, or mixed in a natural or synthetic oil adjusted to an alkaline pH, such that the chemical agent immediately reacts with the exposed, pretreated tissue surface resulting in covalent bonding of the pendant chemical moiety to the deprotonated ε-amino groups of lysine residues on exposed proteins; (5) thorough rinsing of the total tissue surface to remove unreacted chemical agent. This treatment results in masking the deprotonated free amino group with the desired pendant group to alter the net charge and the net charge density of the treated tissue. The predominant protein to react with the acetylation chemicals is collagen. However there are barriers to effective acetylation of the dermal layer of skin, particularly diffusion of the acetylation composition through the stratum corneum and epithelium.

If the acetylation agent is applied in an alkaline buffer solution or aqueous solution, a pH indicator may be added to the buffer to monitor the pH change during mixing and subsequent application. Such pH indicators include phenolphthalein, trimethylphenolphthalein, etc. which change from a colored from to a clear, colorless form at the pH normally found on the skin. It is important to ensure that the acetylation agent is applied to the skin surface before it converts to an inactive, acid form.

It is preferable to pre-treat intact skin by first applying an effective penetration enhancer or first ablating or puncturing the stratum corneum before applying the acetylation agents since penetration is dramatically inhibited by an intact stratum corneum layer. For skin rejuvenation, acetylation agents are applied to increase the net negative charge and the net charge density resulting in an increase in dermal tissue thickness with increased pliability. This treatment results in rejuvenation of thin, brittle skin.

Figure 2:
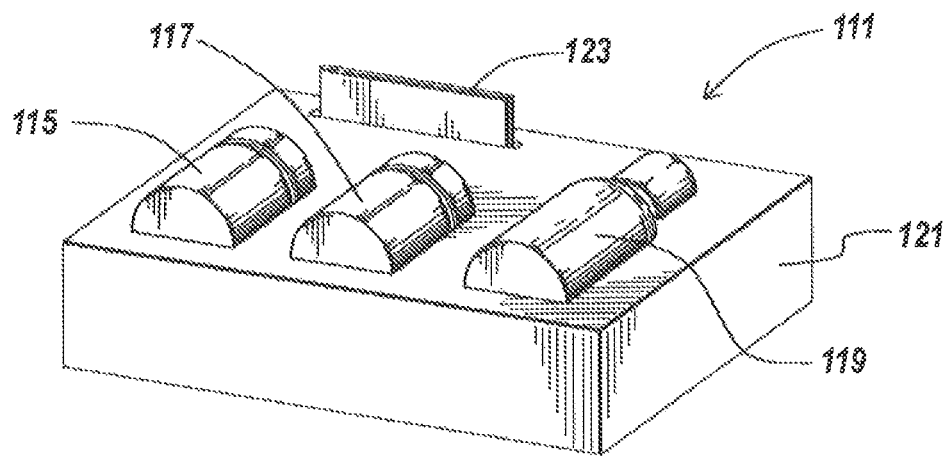
FIG. 2 depicts an article of manufacture embodying features of the present invention; and, FIG. 3 depicts an article of manufacture embodying features of the present invention.

One embodiment features a kit to provide convenience and control. Turning now to FIG. 2, a kit embodying features of the present invention is generally designated by the numeral 111. The kit 111 has a first containment vessel 115 holding a pretreatment solution, a second containment vessel 117 holding the acetylation agent in powder form (or if liquid, in liquid form), and a device 119 for rapidly dissolving or mixing the acetylation agent with the treatment solution as it is applied to the skin. The kit 111 has packaging, in the form of box 121, and instructions 123 for performing the method. Other suitable packaging may comprise plastic wraps, bags, ties and the like.

Figure 3:
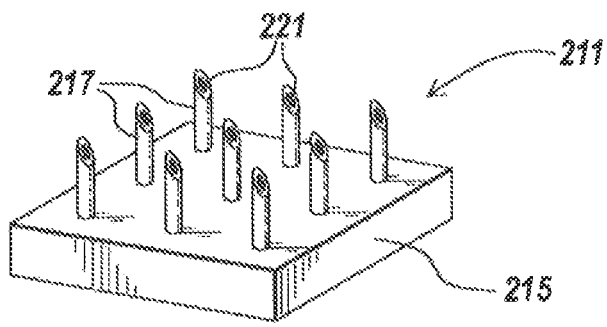

The present invention provides methods for selectively treating intact skin, preferably following ablation or needle puncture of stratum corneum, in a controlled manner to alter the net charge and net charge density of reacted tissues and tissue surfaces to provide specific therapeutic benefits or to rejuvenate skin degenerated by aging and disease. FIG. 3 depicts a micro-needle array, generally designated by the numeral 211 for administration of an acetylation agent. The micro-needle array 211 may comprise a component of the kit 111 of FIG. 2 but is not shown. The micro-needle array 211 has backing 215 for holding the drug and has needles 217 having opening 221 for administering drug to collagen as the micro-needle array 41 is pressed against the skin.

The present invention describes methods for applying specific acetylation agents to intact skin for delivery to dermal tissue, following pretreatment to ablate or puncture stratum corneum and epithelium, followed by treatment with a slightly alkaline solution and subsequent topical application of acetylation agents in alkaline buffer or in oils or penetration enhancers, to react with deprotonated free amines on tissue proteins, thereby altering the net charge characteristics and charge density of the reacted tissue.

In general, the acetylation agent may include agents in the form of sulfonic acids, anhydrides, sulfonyl chlorides, and acid chlorides. Concentrations of the acetylation agents range from 0.1 mg/mL to 100 mg/mL, preferably from 10 mg/mL to 50 mg/mL.

Prior to addition of the acetylation reagent, the intact skin is subject to dermabrasion or micro-needle puncture or pretreated with a penetration enhancer composition such as EDTA, pretreated for 30 seconds to 1 minute with a solution exhibiting a pH from 7.5-9.5. The solution may be composed of a single component, such as disodium phosphate or sodium pyrophosphate or sodium borate, or may be a buffer composition providing a pH ranging from 7.5-9.5. The concentration of the alkaline solution ranges from 0.01M to 0.2M. The acetylation agent is then quickly dissolved in alkaline buffer (0.1-0.35M) or alkaline solution at concentrations ranging from 10-100 mg/mL followed by immediate delivery to the pretreated skin surface by topical administration. The buffer solution may contain a pH indicator to monitor the reduction in pH to the point in which the acetylation agent is no longer active. The acetylation agent may also be mixed with an oil or other penetration enhance carrier, including an oil adjusted to an alkaline pH by addition of solid sodium hydroxide to bring the pH to a range from 8.0-10.0, for example, corn oil adjusted to a pH of 9.1. The skin surface is then rinsed using sterile water or physiological saline. It may be necessary to repeat the treatment steps more than one time to produce optimal affects.

It is preferred that the materials and solutions for this novel skin treatment be contained in kit form to simplify application and allow application by individuals desiring skin rejuvenation. In the most simple form, the kit will contain a vial containing the pretreatment buffer or solution, a sealed vial containing the active acetylation agent, a vial containing the mixing solution (e.g. alkaline buffer, oil, or penetration enhancer solution) for the acetylation agent powder (or liquid), a pipette for adding the mixing solution to the acetylation agent, application pads, and a dermabrasion instrument or micro-needle roller to dermabrade the skin sites before treatment. Aqueous mixing solutions may also contain a pH indicator such as phenolphthalein.

The kit may also contain a device for effective mixing or dissolving of the acetylation agent during delivery to control treatment effectiveness. This device might be as simple as porous patch containing a predetermined quantity of the acetylation agent powder that is placed on the treatment site following application of the pretreatment solution followed by application of a predetermined volume of the treatment solution to wet the patch to dissolve the acetylation agent powder as it penetrates the pretreated skin site. The patch will be packaged in a moisture resistant pouch to prevent hydrolysis that occurs when the acetylation agent is exposed to moisture, including moisture in air. Using this system, the active acetylation agent is delivered as it dissolves and will maintain activity for a longer time than if pre-dissolved in treatment solution and then delivered to the treatment site.

Another application device will use a jet spray device (JetPeel) to deliver the active agent as it dissolves in the alkaline pH treatment solution. The acetylation powder and treatment solution mix in the spray container to dissolve the GA powder as it sprays the skin treatment site under pressure. The pressurized spray also forces the skin channels to open for effective delivery of the soluble GA to the collagen dermal matrix.

The features and other details of the invention will now be more particularly described and pointed out in the following examples describing preferred techniques and experimental results. These examples are provided for the purpose of illustrating the invention and should not be construed as limiting.

EXAMPLES

Rejuvenation of Human Skin

Example 1

Acetylation of Processed Human Skin (Epithelium Removed)

Processed human skin was obtained for treatment. The processed skin was comprised of lyophilized dermis. Two samples were tested, two 2 cm×4 cm specimens. One of specimens was treated with 100 mg/mL of glutaric anhydride. The second specimen was treated with buffer solution alone. The rejuvenation agent was prepared in dilute alkaline buffer solution, pH 8.5, quickly dissolved and applied to the dermis within 15 seconds. Prior to treatment with the active agent, skin specimens were pre-treated with buffer alone. Treatments were completed in 1-minute. Results of the mechanical properties of the specimens are shown in the following Table.

TABLE 1

| Effects of Acetylation Treatment on the Properties of Processed Human Dermis | |
|---|---|
| Parameter | Change |
| Low Chord Modulus | 50.5% decrease |
| Durometer | 5.3% increase |
| Water Retention | 66.8% increase |
| Thickness | 18.3% increase |

As shown in Table 1, the treatment enables the tissue to bind more water and it swells as a result.

The decrease of the low chord modulus signifies the softening of the tissue. This is the stiffness of the tissue at low forces, so this result is indicative of the "feel" of the tissue at forces that would commonly be experienced in normal human motion.

Example 2

Acetylation of Human Skin Without Dermabrasion, Micro-Needle Roll, or Pre-Treatment with Penetration Enhancers In this example, the pre-treatment buffer, 0.1M disodium phosphate solution, pH 8.3, was applied for 30 seconds using surgical gauze. Glutaric anhydride (20 mg/mL) was mixed in 0.3M disodium phosphate solution at pH 8.9 and immediately (less than 5 seconds after dissolution) applied to the defects for 30 seconds to 1 minute using surgical gauze. Treatment sites were then rinsed with 0.1M phosphate buffered saline, pH 7.2. No effect on skin thickness or appearance was noted.

Example 2

Acetylation of Human Skin Following Dermabrasion

In this example, glutaric anhydride was applied to temporal defects adjacent to periorbital areas. Skin defects were first subject to gentle dermabrasion followed by application of 0.1M disodium phosphate solution, pH 8.3 for 30 seconds using surgical gauze. Glutaric anhydride (20 mg/mL) was mixed in 0.3M disodium phosphate solution at pH 8.9 and immediately (less than 5 seconds after dissolution) applied to the defects for 30 seconds to 1 minute using surgical gauze. Treatment sites were then rinsed with 0.1M phosphate buffered saline, pH 7.2. Pre-treatment and post-treatment photos were taken and the results evaluated. The results demonstrated improvement in the appearance of skin defects.

Example 3

Acetylation of Human Skin (Hand and Temple) Following Dermabrasion

In this example, glutaric anhydride was applied to temporal defects adjacent to periorbital areas. Skin defects were first subject to gentle dermabrasion followed by application of 0.1M disodium phosphate solution, pH 8.3 for 30 seconds using surgical gauze. Glutaric anhydride (50 mg/mL) was dissolved in ethanol or anhydrous alcohol and applied to the defects for 1 minute using surgical gauze. Treatment sites were then rinsed with 0.1M phosphate buffered saline, pH 7.2. Up to 5 treatments were made to specific skin sites.

Results demonstrated a visual improvement in skin appearance and a tactile increase in skin thickness at the treatment sites.

Example 4

Acetylation of Human Skin (Temple Area) Following Dermabrasion

In this example, glutaric anhydride was applied to temporal defects adjacent to periorbital areas. Skin defects were first subject to gentle dermabrasion followed by application of 0.1M disodium phosphate solution, pH 8.3 for 30 seconds using surgical gauze. Glutaric anhydride (50 mg/mL) was dissolved in ethanol. Aliquots of approximately 0.25 mL were applied to the defects for 1 minute using surgical gauze. Treatment sites were then rinsed with 0.1M phosphate buffered saline, pH 7.2. Up to 5 treatments were made to specific skin sites Results showed a visual improvement in skin smoothness and a tactile increase in skin thickness at the treatment sites.

Example 5

Acetylation of Human Skin Using Alcohol Penetration Enhancer

In this example, glutaric anhydride was applied to temporal defects adjacent to periorbital areas. Skin defects were pretreated by application of 0.1M disodium phosphate solution, pH 8.3 for 30 seconds using surgical gauze. Glutaric anhydride (50 mg/mL) was dissolved in ethanol and applied to the defects for 1 minute using surgical gauze. Treatment sites were then rinsed with 0.1M phosphate buffered saline, pH 7.2. Up to 5 treatments were made to specific skin sites Results showed a minor visual improvement in skin smoothness and a tactile increase in skin thickness at the treatment sites.

Example 5

Acetylation of Human Skin Using Glutaric Anhydride Powder Without Dermabrasion

In this example, glutaric anhydride was applied to temporal defects adjacent to periorbital areas. Skin defects were pretreated by application of 0.1M disodium phosphate solution, pH 8.3 for 30 seconds using surgical gauze. Glutaric anhydride powder (10 mg/mL) was gently applied to the wet defects for 1 minute, or until the powder dissolved, using surgical gauze. The powder Treatment sites were then rinsed with 0.1M phosphate buffered saline, pH 7.2. Up to 5 treatments were made to specific skin sites No visual improvement in skin smoothness and a tactile increase in skin as observed at the treatment sites.

Example 6

Acetylation of Human Skin Using Glutaric Anhydride in Vegetable Oil Without Dermabrasion In this example, glutaric anhydride was applied to temporal defects adjacent to periorbital areas. Skin defects were pretreated by application of 0.1M disodium phosphate solution, pH 8.3 for 30 seconds using surgical gauze. Glutaric anhydride powder (30 mg/mL) was dispersed in vegetable oil and gently applied to the wet defects for 1 minute using surgical gauze. The treatment sites were then rinsed with 0.1M phosphate buffered saline, pH 7.2. Only one treatment was made to temporal skin sites. Treated sites had a mild tingly feeling immediately after treatment and for sometime after. The application sites also felt thicker and softer.

The applied sites showed a minor visual improvement in skin smoothness and a tactile increase in skin thickness at the treatment sites.

Example 6

Acetylation of Human Skin Using Glutaric Anhydride in pH Adjusted Vegetable Oil Without Dermabrasion In this example, glutaric anhydride was applied to temporal defects adjacent to periorbital areas. Skin defects were pretreated by application of 0.1M disodium phosphate solution, pH 8.3 for 30 seconds using surgical gauze. Glutaric anhydride powder (30 mg/mL) was dispersed in vegetable oil adjusted to a pH of 9.0 using 10N NaOH and gently applied to the wet defects for 1 minute using surgical gauze. The treatment sites were then rinsed with 0.1M phosphate buffered saline, pH 7.2. Only one treatment was made to temporal skin sites. Treated sites had a mild tingly feeling immediately after treatment and for sometime after. The application sites also felt thicker and softer.

The applied sites Results showed a visual improvement in skin smoothness and a tactile increase in skin thickness at the treatment sites.

Example 7

Acetylation of Human Skin Using Glutaric Anhydride in pH Adjusted Vegetable Oil Following Micro-Needle Roller Treatment In this example, glutaric anhydride was applied to the forearm. A skin area approximately 4 mm×4 mm was punctured using a micro-needle roller, followed by pre-treated with 0.1M disodium phosphate solution, pH 8.3 for 30 seconds using cotton swab. Glutaric anhydride powder (40 mg/mL) was dispersed in vegetable oil that was adjusted to a pH of 9.1 using granules of sodium hydroxide powder and gently applied to the pre-treated skin area for 1 minute using a cotton swab. The sites were rinsed using an alcohol swab. Treated sites were slightly red in color and had a mild tingly feeling immediately after treatment and for sometime after. The application site felt thicker immediately after treatment and for several days later.

The applied sites exhibited a tactile increase in skin thickness at the treatment sites.

Example 8

Acetylation of Human Skin Using Glutaric Anhydride in Alkaline Buffer Solution Following Micro-Needle Roller Treatment In this example, glutaric anhydride was applied to the forearm. A skin area approximately 4 mm×4 mm was punctured using a micro-needle roller, followed by pre-treated with 0.1M sodium phosphate buffer, pH 8.3 for 30 seconds using cotton swab. Glutaric anhydride powder (40 mg/mL) was dissolved in 0.3M disodium phosphate solution, pH 9.1 and gently applied to the pre-treated skin area for 1 minute using a cotton swab. The sites were final rinsed using an alcohol swab. Treated sites were slightly red in color and had a mild tingly feeling immediately after treatment. The application site felt slightly thicker immediately after treatment only. Repeated treatments appeared to enhance beneficial results on skin appearance.

Example 9

Acetylation of Human Skin Using Glutaric Anhydride in Alkaline EDTA Solution Following Pretreatment with Alkaline EDTA Solution In this example, glutaric anhydride was applied to the cheek. An area of the upper cheek, below the eye, was pretreated with pH adjusted 0.035M disodium EDTA (pH 9.0) applied using a gauze pad. Glutaric anhydride powder was finely ground using a mortar and pestle and rubbed into a second gauze pad. The gauze was placed on the treatment area and flushed with pH adjusted 0.035M disodium EDTA (pH 9.0) to deliver the glutaric anhydride to the treatment site as it dissolved in the EDTA solution. A slight burning or tingly sensation was noted as the glutaric anhydride penetrated the skin. Some redness was observed at the treatment site after the gauze pad was removed and the site flushed with sterile phosphate buffered saline at pH 7.2. Two such applications were performed. After the second application, an obvious minor skin thickening at the treatment site was observed and persisted for more than 2 weeks.

Example 10

Acetylation of Human Skin Using Glutaric Anhydride Delivered Using Jet Spray (Prophetic)

In this example, glutaric anhydride is applied to skin using a jet spray device. An area of the forearm is pretreated with alkaline pH solution (pH 8.5) using a gauze pad. Glutaric anhydride powder was finely ground using a mortar and pestle and placed in one chamber of the jet spray device. Alkaline pH treatment solution (pH 9.0) is placed in the second chamber of the jet spray device. The jet spray device is activated to mix and dissolve the glutaric anhydride powder in the treatment solution as it is sprayed on the pretreated skin surface. A slight burning or tingly sensation is noted as the glutaric anhydride penetrates the skin. Some redness is observed at the treatment site after the site is flushed with sterile phosphate buffered saline at pH 7.2. Obvious skin thickening and pliability is noted immediately after application.

OTHER EMBODIMENTS

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention herein. Such equivalents are intended to be encompassed in the scope of the present invention.

All references, including patents, publications, and patent applications, mentioned in this specification are herein incorporated by reference in the same extent as if each independent publication, patent or patent application was specifically and individually indicated to be incorporated by reference.

The invention claimed is:

1. A method of treating dermis in vivo comprising the steps of:
   topically pretreating an area of skin in a subject with dermal abrasion and with one or more penetration devices configured to ablate or puncture stratum corneum and epithelium, wherein the one or more penetration devices comprise microneedles;
   further topically pretreating the exposed tissue surface with alkaline buffer solution for 30 seconds to 2 minutes to bring the pH of the tissue surface to between 7.5 and 9.5; and
   topically applying to said area of skin an effective amount of an acylation agent to increase one or more skin characteristics consisting of at least one selected from the group consisting of: hydration, pliability and thickness, wherein the acylation agent is selected from the group consisting of: glutaric anhydride, succinic anhydride, methyl glutaric anhydride, maleic anhydride, pthalic anhydride, and mixtures and combinations thereof.

2. The method of claim 1, wherein said step of topically pretreating with dermal abrasion and penetration devices further comprises one or more skin pretreatments selected from the group consisting of abrasive washes and air jet injection.

3. The method of claim 1, wherein said effective amount of an acylation agent is in a delivery system selected from the group consisting of foams, ointments, pastes, oils, creams, solutions, tinctures, gels, suspensions, powders, aerosols and emulsions.

4. The method of claim 3, wherein said delivery system has an aqueous base and said acylation agent is held in a buffered solution at a pH of 8.0 to 10.0.

5. The method of claim 3, wherein said delivery system has an oil base and said acylation agent is held as a suspension.

6. The method of claim 4, wherein said acylation agent has a concentration in said aqueous base of 1 to 100 mg/ml.

7. The method of claim 3, wherein said delivery system has an alcohol base and said acylation agent has a concentration of 1 to 100 mg/ml.

8. The method of claim 5, wherein said acylation agent has a concentration of 1 to 100 mg/ml.

9. The method of claim 3, wherein said delivery system has a penetration enhancer.

10. The method of claim 9, wherein said penetration enhancer is at least one selected from the group consisting of: ethylenediaminetetraacetic acid and salts thereof.

11. The method of claim 10, wherein said penetration enhancer is present in a concentration of 0.022 M to 0.040 M.

12. The method of claim 1, further comprising one or more post application treatments comprising the application of one or more washes.

13. The method of claim 12, wherein said one or more washes is selected from the group of solutions consisting of: aqueous solutions, phosphate buffered solutions, saline solutions and surfactant solutions and combinations thereof.

14. The method of claim 1, wherein said acylation agent is glutaric anhydride.

15. The method of claim 1, wherein said acylation agent is glutaric anhydride or methyl glutaric anhydride held in an aqueous base at a pH of 8.0-10.

16. The method of claim 1, wherein said acylation agent is glutaric anhydride or methyl glutaric anhydride held in an oil base.

17. A method of treating dermis in vivo comprising the steps of:
topically pretreating an area of skin in a subject with dermal abrasion and with one or more penetration devices configured to ablate or puncture stratum corneum and epithelium, wherein the one or more penetration devices comprise microneedles;
further topically pretreating the exposed tissue surface with alkaline buffer solution for 30 seconds to 2 minutes to bring the pH of the tissue surface to between 7.5 and 9.5; and topically applying to said area of skin an effective amount of an acylation agent to increase net charge and net charge density in the dermis, wherein the acylation agent is selected from the group consisting of: glutaric anhydride, succinic anhydride, methyl glutaric anhydride, maleic anhydride, pthalic anhydride, and mixtures and combinations thereof.

18. The method of claim 17, wherein said step of topically pretreating with dermal abrasion and penetration devices further comprises one or more skin pretreatments selected from the group consisting of abrasive washes and air jet injection.

19. The method of claim 17, wherein said effective amount of an acylation agent is in a delivery system selected from the group consisting of foams, ointments, pastes, oils, creams, solutions, tinctures, gels, suspensions, powders, aerosols and emulsions.

20. The method of claim 19, wherein said delivery system has an aqueous base and said acylation agent is held in a buffered solution at a pH of 8.0 to 10.0.

21. The method of claim 1, wherein topically applying to said area of skin an effective amount of an acylation agent comprises applying the acylation agent to natural dermal collagen under reaction conditions to react said natural dermal collagen with said acylation agent to form a modified collagen that increases one or more skin characteristics consisting of at least one selected from the group consisting of: hydration, pliability, and thickness.

22. The method according to claim 17, wherein topically applying to said area of skin an effective amount of an acylation agent comprises applying the acylation agent to natural dermal collagen under reaction conditions to react said natural dermal collagen with said acylation agent to form a modified collagen having higher net charge and higher net charge density than natural dermal collagen.

23. The method of claim 3, wherein said delivery system has an anhydrous base.

24. The method according to claim 23, wherein said acylation agent has a concentration in said anhydrous base of 1 to 100 mg/ml.

* * * * *